United States Patent [19]

Esquivel H.

[11] Patent Number: 4,836,673

[45] Date of Patent: Jun. 6, 1989

[54] WAVELENGTH ACCURACY TEST SOLUTION AND METHOD

[75] Inventor: J. Benjamin Esquivel H., Midland, Mich.

[73] Assignee: The Dow Chemical Company, Midland, Mich.

[21] Appl. No.: 230,670

[22] Filed: Aug. 5, 1988

Related U.S. Application Data

[63] Continuation of Ser. No. 946,251, Dec. 24, 1986, abandoned.

[51] Int. Cl.$^4$ ................................................ G01J 3/00
[52] U.S. Cl. .................................. 356/300; 356/243; 250/252.1; 252/408.1
[58] Field of Search .............................. 356/300, 243; 250/252.1; 252/408.1

[56] References Cited

U.S. PATENT DOCUMENTS

| | | | |
|---|---|---|---|
| 4,106,857 | 8/1978 | Snitzer | 350/311 |
| 4,439,347 | 3/1984 | Sun et al. | 250/252.1 |
| 4,461,718 | 7/1984 | Kaye et al. | 252/408.1 |

OTHER PUBLICATIONS

West et al, "Practical Standards for UV Absorption and Fluorescence Spectrophotometry", *American Laboratory*, vol. 9, No. 3 (Mar. 1977), pp. 37–49.

Moeller, T., and Brantley, J. C., The Rare Earths–Spectrophotometric Estimation of Certain Rare Earth Elements, Mar. 1950, *Analytical Chemistry*, vol. 22, No. 3, pp. 433–441.

Stewart, D. C., and Kato D., Analysis of Rare Earth Mixtures by a Recording Spectrophotometer, Feb. 1958, *Analytical Chemistry*, vol. 30, No. 2, pp. 164–172.

*Primary Examiner*—F. L. Evans
*Attorney, Agent, or Firm*—Timothy S. Stevens

[57] ABSTRACT

A packaged test solution for determining the wavelength accuracy of variable wavelength liquid chromatography spectrophotometric detectors at one or more reference wavelengths consisting of 254.6, 378.9, 522.3, and 652.5 nanometers. The packaged solution comprises a hermetically sealed container of an effective concentration of erbium III ions such as a sealed container of a 0.2 molar solution of erbium III perchlorate in water. The test solution has the required intense absorption bands at the reference wavelengths which additionally do not vary by more than about 0.3 nanometers with the varying bandpass characteristics of such detectors. The invention is also a method comprising filling the cell of the detector with the test solution and varying the indicated wavelength of detection to find the indicated wavelength of maximum absorbance in a wavelength region around one of the reference wavelengths and then calculating the difference between the indicated wavelenth of maximum absorbance and the reference wavelength to determine the accuracy of the indicated wavelength of the detector.

9 Claims, 1 Drawing Sheet

WAVELENGTH ACCURACY TEST SOLUTION AND METHOD

CROSS-REFERENCE TO RELATED APPLICATION

This is a continuation of application Ser. No. 946,251, filed Dec. 24, 1986, now abandoned.

BACKGROUND OF THE INVENTION

The invention is in the field of solutions and methods used to test the accuracy of spectrophotometers and specifically to test the accuracy of wavelength selection of variable wavelength liquid chromatography spectrophotometric detectors.

Liquid chromatography is an important branch of analytical chemistry. Most liquid chromatography systems include a spectrophotometer detector and a high proportion of these detectors are of the type where the wavelength of detection can be selected at will within a given range, i.e. the variable wavelength type of detector. Problems with variable wavelength detectors in liquid chromatography can occur if the actual wavelength of detection is different than the detector's set wavelength. For example, linearity of detection and selectivity of detection can deteriorate if the liquid chromatographic procedure is actually being run at one wavelength while the procedure calls for detection at another wavelength. Even when a variable wavelength detector is accurately calibrated when new, its wavelength accuracy can deteriorate with time. Therefore, there is an important need to determine the accuracy of wavelength selection of variable wavelength liquid chromatography detectors.

The need to check the accuracy of wavelength selection is also important for general laboratory spectrophotometers and specific test solutions have been discovered for the calibration of general laboratory spectrophotometers such as the rare earth ion solution described in U.S. Pat. No. 4,461,718 to Kaye et al. Rare earth compound are generally considered to be excellent candidates for the peparation of accuracy standards for variable wavelength spectrophotometers because solutions of rare earth ions often absorb light in very sharp bands as shown, for example, by Moeller et al. in Volume 22, No. 3, March 1950, pages 433-441 of *Analytical Chemistry* and by Stewart et al. in Volme 30, No. 2, February 1958, pages 164-172 of *Analytical Chemistry*. The patent and literature references, above, are fully incorporated herein by reference.

The prior rare earth test solutions developed for general laboratory spectrophotometers did not provide acceptable perfomance for variable wavelength liquid chromatography detectors because of the different optical characteristics of variable wavelength liquid chromatographic detectors. For example, the optical bandpass of most of these detectors is not adjustable and is different for different detector brands (generally ranging from about 2 nm to about 6 nm). The absorption bands of many rare earth ions in solution shift in absorbance maximum with a variation in optical bandpass, e.g., terbium III shifts form 219.4 to 218.6 nm when the bandpass changes for 2 to 6 nm. Another problem with these detectors is that it is more difficult to locate an absorption maximum by varying the wavelength selector of the detector since variable wavelength liquid chromatography detectors are generally designed to operate at one selected wavelegnth and are not designed to be scanning instruments. Therefore, the absorbance maximum of a test solution for variable wavelength liquid chromatography detectors must be intense or the maximum will not be found (and this is especially true for single beam variable wavelength detectors). For example, the well known holmium III test solution absorbance intensities at 241.1, 278.2 and 287.5 nm are too weak for use with most variable wavelength liquid chromatographic detectors.

The present invention is a packaged test solution and method for determining the wavelength accuracy of a variable wavelength liquid chromatography spectrophotometric detector comprising erbium III ions. The test solution has bands of sufficient intensity at 254.6, 378.9, 522.3, and 652.2 nm. In addition, these bands do not shift more than about 0.3 nm when the optical bandpass varies between 2 and 6 nm.

SUMMARY OF THE INVENTION

The invention is a packaged test solution for determining the wavelength accuracy of a variable wavelength liquid chromatography spectrophotometric detector, comprising a hermetically sealed container filled with an effective concentration of erbium III ions.

The invention is also a method of determining the wavelength accuracy of a variable wavelength liquid chromatography spectrophotometric detector having a flow through detection cell, which method comprises the steps of: (a) flowing a solution of an effective concentration of erbium III ions into the cell; (b) varying the indicated wavelength of the detector to find he indicated wavelength of maximum absorbance of the test solution in the wavelength region around a reference wavelength selected from the group consisting of 254.6 nm, 378.9 nm, 522.3 nm, and 652.5 nm; (c) calculating the difference in units of nm between the indicated wavelength of maximum absorbance of step (b) and the reference wavelength selected in step (b) to determine the accuracy of the detector at the selected wavelength.

DETAILED DESCRIPTION OF THE INVENTION

Figure 1:
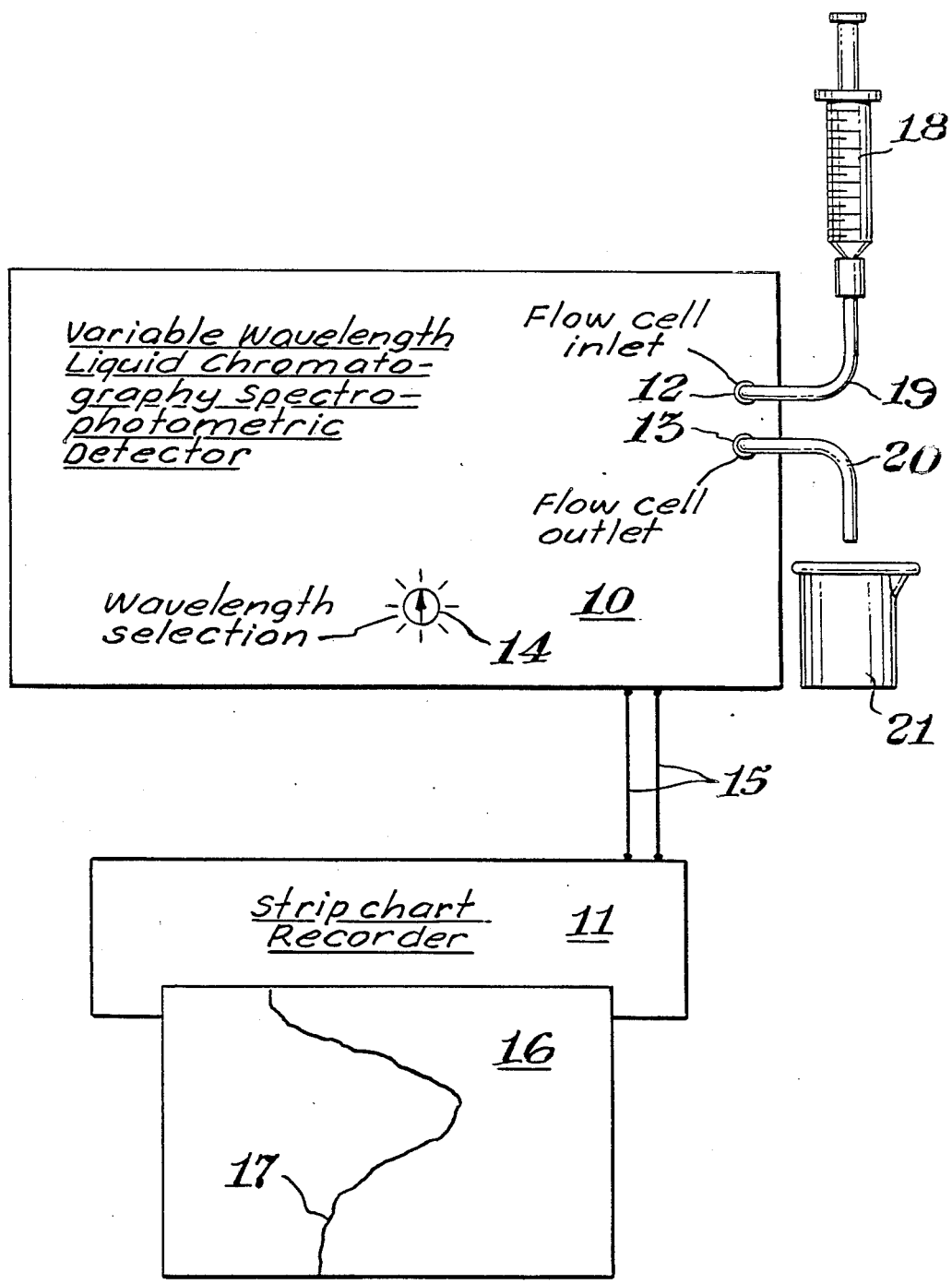
FIG. 1 is a front view of a variable wavelength liquid chromatography spectrophotometric detector and associated strip chart recorder, the detector shown being calibrated according to the present method.

The method of the present invention comprises flowing the test solution into the flow cell of a normally operating variable wavelength liquid chromatography spectrophotometric detector by, for example, first flushing the cell with about 5 ml of water and then with about 1 ml of the test solution using a syringe, leaving the cell filled with the test solution. If the detector is a double beam detector and has a reference cell, the reference cell preferably contains air or water. The test solution allows the testing of the accuracy of the indicated wavelength of the detector at specific reference wavelengths, i.e., 254.6, 378.9, 522.3, and 652.5 nm, which reference wavelengths are believed accurate to within about plus or minus 0.2 nm. The indicated wavelength of the detector is varied in, for example, 0.5 or 1 nm increments around one of the reference wavelengths (for example from 240 to 270 nm) to find the indicated wavelength of maximum absorbance as shown on some detectors by an absorbance window readout or for most any detector by a maximum pen response on a conventional strip chart recorder connected to the detector.

Referring now to FIG. 1, therein is shown a front view of a variable wavelength liquid chromatography spectrophotometric detector 10 and associated strip chart recorder 11, the detector 10 shown in the process of being calibrated according to the present method. The detector 10 has a flow cell inlet 12, a flow cell outlet 13 and a wavelength selection knob 14 calibrated in indicated nm units. The detector 10 and the recorder 11 are connected to each other by wires 15 so that the strip chart 16 produced by the strip chart recorder 11 shows a trace 17 of the absorbance output of the detector 10. A solution of erbium III ions, the solution having a concentration of erbium III ions of more than 0.01 molar, is contained within a syringe 18 and is flowed into the flow cell inlet 12 via a section of tubing 19. Excess solution from the flow cell outlet 13 flows through a tube section 20 into a beaker 21. Then, the wavelength selection knob 14 is rotated to vary the indicated wavelength of detection around a reference wavelength selected from the group consisting of 254.6 nm, 378.9 nm, 522.3 nm, and 652.5 nm, to find the indicated wavelength of maximum absorbance, i.e, the wavelength associated with the highest position of the trace 17. Then, the difference, in units of nm, between the indicated wavelength of maximum absorbance and the reference wavelength is calculated by subtraction to determine the wavelength accuracy of the detector 10 at the selected reference wavelength.

The ease of the determination of the wavelength of maximum absorbance is a function of the intensity of absorption of the test solution for any given detector. Preferably, the intensity of absorption is as high as practical, e.g., the use of about 0.2 molar erbium III. However, not all erbium compounds are soluble enough to generate a 0.2 molar solution of erbium III ions and weaker solutions such as 0.01 molar erbium III have been shown to be satisfactory. The lowest concentration of an erbium III solution that would be an effective concentration is a concentration that just allows the determination of the indicated wavelength of maximum absorbance. Below the lowest concentration of an erbium III ions that would be an effective concentration it is not possible to determine the indicated wavelength of maximum absorbance. The highest concentration of an erbium III solution (in excess of the lowest effective concentration) that would be an effective concentration is generally the solubility limit concentration of the erbium III ions in the test solution. The concentration of erbium III ions should not be so high in the test solution that the absorbance at a reference wavelength is above 2. Preferably, the erbium III compound used is erbium III perchlorate which has a relatively high solubility and results in test solutions that are stable upon extended storage ion a hermetically sealed container. However, erbium III chloride is satisfactory even though it is not as soluble as the perchlorate compound and does not result in as stable a solution. Preferably, the anion of the erbium III cation is transparent in the test solution at the reference wavelengths. However, the anion can absorb some light at the reference wavelengths as long as the concentration of erbium III ions is an effective concentration. Water is the preferred solvent for the test solution but other solvents alone or mixed with water, such as methanol, can be used. Mineral acids, such as hydrochloric acid, may be added to the solution to enhance the solubility of an erbium III compound (for example erbium III oxide can be dissolved in perchloric acid). Test solutions comprising an explosive composition of perchloric acid and an organic solvent such as methanol are not recommended. Most preferably, the test solution is an aqueous solution of about 0.2 molar erbium III perchlorate in water.

The indicated wavelength of maximum absorbance of the test solution is compared to the reference wavelength of the test solution to determine the wavelength accuracy of the detector. For example, if the indicated wavelength of maximum absorbance of the test solution is 258.5 nm then the detector is inaccurate by 258.5 nm−254.6 nm or about 4 nm at 254.6 nm.

The test solution of the present invention can be prepared for use at a later time. The test solution in this event should be packaged in a hermetically sealed container in order to ensure the integrity of the solution. Preferably, the sealed container is a borosilicate glass vial having a Teflon ® lined screw cap (such as vial number H3528 and cap number H3573 available from the Anspec Co., Ann Arbor, Mich.) which vial and cap are specifically designed and recognized for the storage of reagents and standards. Another preferred sealed container is a borosilicate glass vial having a Teflon lined crimped septum (such as vial number H3579, septum number A3284 and crimp collar A4697, available from the Anspec Co.). Containers comprising materials other than borisilicate glass and Teflon can also be used such as various plastic bottles and caps as long as they are not chemically attacked by the test solution and do not result in contamination of the test solution by, for example, the leaching of a contaminate from the container that would significantly interfere at a reference wavelength of the test solution. The hermetically sealed container should be labeled as to its contents. In addition, the label can contain instructions of the use of the contents to determine the wavelength accuracy of a variable wavelength liquid chromatography detector.

EXAMPLE

A 0.2 molar erbium III perchlorate solution is prepared in water using Alpha Products 99.9% grade erbium III perchlorate hexahydrate dissolved in Fisher Scientific Co. HPLC grade water and 15 ml of the solution is placed in a 20 ml borosilicate glass vial and the vial is sealed shut with a Teflon lined cap. This packaged test solution is then opened and used to determine the wavelength accuracy of the variable wavelength liquid chromatographic detectors listed in Table I using the procedure given in the Detailed Description Of The Invention.

TABLE I

INDICATED WAVELENGTH OF MAXIMUM ABSORBANCE AND WAVELENGTH ACCURACY FOR REPRESENTATIVE VARIABLE WAVELENGTH LIQUID CHROMATOGRAPHY DETECTORS

| DETECTOR | nm | nm | nm | nm |
| --- | --- | --- | --- | --- |
| Kratos 773 | 254.7 | 380.0 | nd | nd |
| S.N. 778YCBT | (0.1) | (1.1) | | |
| Kratos 773 | 252.5 | 377.0 | 520.7 | nd |
| S.N. 836TCLB | (2.1) | (1.9) | (1.6) | |
| Perkin Elmer LC-95 | 253.0 | 379.0 | nd | nd |
| S.N. 51971 | (1.6) | (0.1) | | |
| Perkin Elmer LC-55 | 254.5 | 379.0 | nd | nd |
| S.N. 3361 | (0.1) | (0.1) | | |
| LKB 2140 | 255.0 | nd | nd | nd |
| S.N. 418 | (0.4) | | | |
| Kratos 773 | 259.5 | 384.0 | 528.0 | 655.0 |

TABLE I-continued
INDICATED WAVELENGTH OF MAXIMUM ABSORBANCE AND WAVELENGTH ACCURACY FOR REPRESENTATIVE VARIABLE WAVELENGTH LIQUID CHROMATOGRAPHY DETECTORS

| DETECTOR | nm | nm | nm | nm |
|---|---|---|---|---|
| S.N. 226TSBC | (4.9) | (4.1) | (5.7) | (2.5) |
| Kratos 773 | 258.0 | 382.0 | 526.2 | 652.5 |
| S.N. 2079TKBS | (3.4) | (3.1) | (3.9) | (0) |
| Varian UV-200 | 254.0 | 379.0 | 523.0 | 653.0 |
| S.N. 0184 | (0.6) | (0.1) | (0.7) | (0.5) |
| Hewlett Packard 1040 | 254.5 | 378.5 | 522.5 | nd |
| S.N. 2606A00149 | (0.1) | (0.4) | (0.2) | |
| Kratos 783 | 256.5 | 381.0 | 524.0 | nd |
| S.N. 1863TMBA | (0.9) | (2.1) | (1.7) | |
| Reference wavelength of the test solution | 254.6 | 378.9 | 522.3 | 652.5 | nd, not determined; numbers in ( ) represent the absolute value of the difference between the indicated wavelength of maximum absorbance and the reference wavelength of the test solution; numbers in ( ) of more than about 0.5 nm are significant.

The data in Table I show that the packaged test solution and method of the present invention are applicable for a wide range of variable wavelength liquid chromatography detectors.

What is claimed is:

1. A method for determining the wavelength accuracy of a variable wavelength liquid chromatography spectrophotometric detector having a flow thorugh detection cell, an optical bandpass of from 2 to 6 nm and a means to vary the indicated wavelength of detection, which method comprises the steps of:
   (a) flowing a liquid solution of erbium III ions into the cell, the solution having a concentration or erbium III ions of more than 0.01 molar;
   (b) varying the indicated wavelength of detection of the detector to find the indicated wavelength of maximum absorbance of the solution in a wavelength region around a reference wavelength selected from the group consisting of 254.6 nm, 378.9 nm, 522.3 nm, and 652.5 nm, with a wavelength shift of plus or minus 0.3 nm or less around these reference wavelengths despite the optical bandpass of from 2 to 6 nm of the detector; and
   (c) calculating the difference, in units of nm, between the indicated wavelength of maximum absorbance of step (b) and the reference wavelength selected in step (b) to determine the accuracy of the detector at the wavelength selected in step (b), the concentration of erbium III ions in excess of 0.01 molar effective to result in the ability to perform step (b) without the maximum absorbance exceeding 2.

2. The method of claim 1 wherein the erbium III ions are generated from erbium III perchlorate.

3. The method of claim 2 wherein the solution is an aqueous solution.

4. The solution of claim 1 wherein the concentration of erbium III is greater than about 0.05 molar.

5. The method of claim 4 wherein the erbium III ions are generated from erbium III perchlorate.

6. The method of claim 5 wherein the solution is an aqueous solution.

7. The method of claim 1 wherein the concentration of erbium III is greater than about 0.1 molar.

8. The method of claim 7 wherein the erbium III ions are generated from erbium III perchlorate.

9. The method of claim 8 wherein the solution is an aqueous solution.

* * * * *

UNITED STATES PATENT AND TRADEMARK OFFICE
CERTIFICATE OF CORRECTION

PATENT NO. : 4,836,673
DATED : June 6, 1989
INVENTOR(S) : J. Benjamin Esquivel H.

It is certified that error appears in the above-identified patent and that said Letters Patent is hereby corrected as shown below:

Col. 1, line 41, delete "compound" and insert --compounds--;
       line 42, delete "peparation" and insert --preparation--;
       line 47, delete "Volme" and insert --Volume--;
       line 53, delete "perfomance" and insert --performance--;
       line 62, delete "form" and insert --from--;
       line 63, delete "for" and insert --from--;
       line 68, delete "wavelegnth" and insert --wavelength--.
Col. 2, line 15, delete "652.2" and insert --652.5--;
       line 32, delete "he" and insert --the--.
Col. 3, line 57, delete "ion" and insert --in--.
Col. 4, line 37, first occurrence, delete "of" and insert --for--.
Col. 5, line 33, delete "or" and insert --of--.
Col. 6, line 22, Claim 4, delete "solution" and insert --method--.

Signed and Sealed this

Thirteenth Day of November, 1990

Attest:

HARRY F. MANBECK, JR.

*Attesting Officer*      *Commissioner of Patents and Trademarks*